US005893374A

United States Patent [19]

Decareau

[11] Patent Number: 5,893,374
[45] Date of Patent: Apr. 13, 1999

[54] PERMANENT WAVE END PAPER IMPREGNATED WITH A PH INDICATOR AND METHOD

[76] Inventor: Wendy M. Decareau, Two Schooner Ridge. Marblehead, Mass. 01945

[21] Appl. No.: 08/979,423

[22] Filed: Nov. 24, 1997

[51] Int. Cl.$^6$ ............................................. A45D 7/04
[52] U.S. Cl. ........................ 132/207; 132/222; 132/221
[58] Field of Search .............................. 132/204, 205, 132/207, 222, 221, 206

[56] References Cited

U.S. PATENT DOCUMENTS

| | | | |
|---|---|---|---|
| 2,529,886 | 11/1950 | Semco | 132/205 |
| 2,991,790 | 7/1961 | Bonilla | 132/205 |
| 4,098,577 | 7/1978 | Halpern | 436/1 |
| 4,398,183 | 8/1983 | Ando . | |
| 4,655,377 | 4/1987 | Orangeo, Jr. et al. . | |
| 4,962,775 | 10/1990 | Squatrito . | |
| 5,047,206 | 9/1991 | Dombrowski . | |
| 5,085,216 | 2/1992 | Henley, Jr. et al. | 600/367 |
| 5,121,762 | 6/1992 | DiPinto et al. | 132/204 |
| 5,217,444 | 6/1993 | Schoenfeld | 604/361 |
| 5,267,532 | 12/1993 | Franklin et al. . | |
| 5,378,454 | 1/1995 | Burmeister | 132/205 |
| 5,533,532 | 7/1996 | Hawkins et al. | 132/204 |

FOREIGN PATENT DOCUMENTS

| | | | |
|---|---|---|---|
| 366721 | 2/1932 | United Kingdom | 132/221 |
| 465881 | 5/1937 | United Kingdom | 132/221 |

*Primary Examiner*—John J. Wilson
*Assistant Examiner*—Eduardo C. Robert
*Attorney, Agent, or Firm*—O'Connell Law Firm

[57] ABSTRACT

A permanent wave end paper comprising an absorbent paper impregnated with at least one pH indicator whereby, when a length of hair to be permanently waved is rolled with a strip of the permanent wave end paper, the strip of permanent wave end paper exhibits a chromatic indication of whether the strip of permanent wave end paper and the length of hair have been saturated with a permanent wave liquid chemical. The permanent wave end paper may comprise a high purity cellulose paper impregnated with a wet strength resin such as urea formaldehyde or melamine. The permanent wave end paper may be included in a kit for imparting a permanent wave to hair that comprises in addition to at least one strip of permanent wave end paper a permanent wave lotion and a permanent wave neutralizing agent. The permanent wave kit may be employed in practicing the process of the invention wherein a strip of permanent wave end paper is disposed against a length of hair to be permanently waved, the length of hair is arranged in a desired configuration, the length of hair and the strip of permanent wave end paper are saturated with a portion of the volume of permanent wave lotion, a sufficient period of time is allowed to pass to allow the permanent wave lotion to rupture at least some of the cystine sulfur to sulfur bonds in the length of hair, and the length of hair and the strip of permanent wave end paper are saturated with a portion of the volume of permanent wave neutralizing agent.

24 Claims, 2 Drawing Sheets

5,893,374

PERMANENT WAVE END PAPER IMPREGNATED WITH A PH INDICATOR AND METHOD

FIELD OF THE INVENTION

This invention relates generally to hairdressing. More particularly, it relates to a permanent wave end paper that changes color in response to a change in pH thereby providing a user with a visual indication as to whether the permanent wave end paper has been completely saturated with a permanent wave liquid chemical.

BACKGROUND OF THE INVENTION

Stated most simply, permanent wave hair dressing is accomplished by rolling a length of hair onto a roller, applying a first liquid chemical to the hair to induce a permanent wave, allowing a length of time to pass, and then applying a second liquid chemical to the hair to stop the permanent waving action of the first liquid chemical. Normally, a segment of paper is rolled along with at least the end of each length of hair to protect the hair from frizzing and the like during the permanent wave process. Appropriately, this paper is commonly referred to as end paper.

It is important to note that there are variables that affect the condition of permanent waves such as differences in hair properties including hair condition and health, the type of permanent wave liquid chemical used, temperature and time, and hairdresser skill and experience. Unfortunately, these factors are not easily controllable. During permanent waving, the condition of the waves must be ensured by feel and observation and is directly related to the proper and thorough saturation of the end papers with the respective permanent wave liquid chemical during application by the hair dresser. If the end papers are not sufficiently and uniformly saturated, the resulting permanent wave will be incomplete or otherwise unacceptable.

Such imperfections are a common occurrence because with presently available end paper it is difficult to observe and determine when the end papers are fully saturated since there is no clear visual differentiation between wet and dry portions of the end paper. For example, where a prior art strip of end paper is white in color, there is substantially no difference in appearance between a wet and a dry portion of a piece of end paper. This problem is particularly prevalent when multiple liquid chemicals are applied during the hair dressing process such as with the application of a permanent wave lotion followed by a permanent wave neutralizing agent. Hairdressers typically must rely on experience and judgment to determine whether hair has been adequately saturated with the permanent wave lotion and the permanent wave neutralizing agent. This reliance often results in either over or under application of the respective liquid chemical with a multiplicity of consequent disadvantages. For example, there may be a waste of liquid chemical, poor wave quality, an increase in hairdressing time, as well as customer dissatisfaction.

Certainly one knowledgeable in the art will be aware that the prior art has attempted to provide indications of the completion of a permanent wave process. For example, in U.S. Pat. No. 4,398,183 to Ando, a lead acetate paper is located adjacent hair undergoing a permanent wave, and a complex detecting apparatus with a light emitting diode and a light receiving portion triggers a buzzer device when a chemical reaction between the lead acetate paper and a volume of hydrogen sulfide gas emitted by the permanent wave process changes the lead acetate paper from brown to black thereby indicating that the permanent wave is complete. As a result, it becomes clear that the Ando patent presents a complicated, costly, cumbersome and impractical method and device. Furthermore, the Ando apparatus is capable of indicating only whether a permanent wave is complete; there is no indication as to whether a given length of hair has been saturated by a permanent wave liquid chemical. Consequently, the Ando apparatus may provide a positive indication of a complete permanent wave process notwithstanding the fact that one or more permanent wave liquid chemicals have been hopelessly misapplied.

In light of the above, it becomes clear that there is a great need in the art for a permanent wave end paper and method that permit a user to ensure that the permanent wave end paper and thus the length of human hair with which the end paper is rolled have been completely saturated with the permanent wave liquid chemical. Certainly, a permanent wave end paper that is simple in use and economical in manufacture and that would demonstrate a change in color in response to saturation by a permanent wave liquid chemical would be ideal.

SUMMARY OF INVENTION

Advantageously, a principal object of the present invention is to provide a permanent wave end paper and method for providing a visual indication of whether the end paper is saturated with a permanent wave liquid chemical.

A further object of the present invention is to provide such an end paper and method that is simple and convenient in use and economical in manufacture.

Another object of this invention to provide a permanent end wave end paper that changes from a first color to a second color when the permanent wave end paper and length of human hair have been saturated with a permanent lotion and from the second color to a third color in response to the application of a permanent wave neutralizing agent.

An additional object of the invention is to prevent waste of permanent wave chemical solution by indicating to a user when a strip of permanent wave end paper and length of human hair are saturated with the permanent wave liquid chemical.

Still another object of the invention is to provide a kit for imparting a permanent wave to hair that accomplishes the foregoing objects.

Yet a further object of this invention is to provide a method of permanent waving hair utilizing a plurality of strips of permanent wave end paper wherein each strip of end paper is impregnated with a pH indicator that is calibrated to exhibit a chromatic indication in response to an application of a permanent wave liquid chemical whereby, when a strip of permanent wave end paper is associated with a length of hair, a user can ensure that the permanent wave end paper and the length of human hair have been completely saturated with the permanent wave liquid chemical by ensuring that the entire strip of permanent wave end paper demonstrates a change in color in response to the application of the permanent wave liquid chemical.

It is also an object of this invention to provide an apparatus and method that can conveniently and practically detect and indicate the condition of a permanent wave that is easy to use, improves the quality of a permanent wave, and saves time and expense in the permanent wave process.

Still another object of the present invention is to improve the quality and reliability of the permanent waving process by eliminating unnecessary guesswork in determining the saturation condition of a permanent wave.

A related object is to provide such a permanent wave end paper, kit, and method that thereby improves the actual and apparent efficiency and skill of the hairdresser using the invention.

Yet a further object of the invention is to provide a permanent wave end paper, kit, and method that may be used by beauticians as a teaching tool in beauty schools for hairdressing and for animal grooming such as with dogs, particularly poodles, and cats.

In accomplishing the aforementioned objects, an embodiment of the permanent wave end paper according to the present invention essentially comprises an absorbent paper impregnated with a pH indicator that is calibrated to change color in response to an application of a permanent wave liquid chemical when the permanent wave end paper is associated with a length of human hair. Under such an embodiment, a user can visually ensure that the permanent wave end paper and the length of human hair have been completely saturated with the permanent wave liquid chemical by ensuring that the entire strip of permanent wave end paper exhibits a change in color in response to the application of the permanent wave liquid chemical.

In one preferred embodiment, the permanent end wave end paper is a universal indicator paper whereby, when the permanent end wave paper is associated with a length of human hair, the permanent wave end paper clearly changes from a first color to a second color when the permanent wave end paper and length of human hair have been saturated with a permanent wave lotion and the permanent wave end paper changes from the second color to a third color in response to the application of a permanent wave neutralizing agent.

Of course, it should be made clear that within the context of the present disclosure a change in color may comprise a variation in color shades (i.e., a change from light blue to dark blue or a change from pink to red) and need not, but may, comprise a complete change between colors (i.e., a change from red to blue). It should also be clear that the term permanent wave liquid chemical encompasses both permanent wave lotion and permanent wave neutralizing agent.

Since, by the nature of its use, the permanent wave end paper will be subject to relatively significant tensile and other forces, a preferred embodiment of the permanent wave end paper has a wet strength sufficient to withstand a tension of at least about 30 grams applied to a one-half inch wide strip of permanent wave end paper, and a most preferred embodiment of the invention has a wet strength sufficient to withstand a tension of at least about 50 grams applied to a one-half inch wide strip of permanent wave end paper. Although one skilled in the art will be aware of a number of methods for creating a paper with such a wet strength, a presently preferred embodiment of the invention provides a suitable paper in the form of a high purity cellulose paper impregnated with a wet strength resin such as urea formaldehyde and melamine for increasing wet strength and tear resistance.

Ideal paper will have a weight of approximately 16 grams per square meter. Also, ideal paper will be sufficiently thin. For example, the paper should not be thicker than approximately 0.02 inches. Furthermore, an ideal embodiment of the invention will have suitable porosity. For example, non-perforated strips of the present permanent wave end paper preferably demonstrate a Filtrona Pressure Drop of between about 14.1 and 24.2 millimeters of water. In the present disclosure, the term Filtrona Pressure Drop is to be defined as the number of millimeters of water passing through a layer of permanent wave end paper in response to a flow rate of 17.5 cubic centimeters per second.

In another embodiment, the invention comprises a kit for imparting a permanent wave to hair. The kit most basically comprises a permanent wave lotion, a permanent wave neutralizing agent, and at least one strip of permanent wave end paper according to the present invention. Such a permanent wave kit may be employed to practice a method for permanently waving human hair, wherein a user (i.e., a hairdresser) possessed of the materials comprising the kit of the present invention may begin by disposing a strip of permanent wave end paper against a length of hair to be permanent waved. The length of hair then may be arranged in a desired configuration and saturated with a portion of permanent wave lotion for rupturing the cystine sulfur to sulfur bonds that are found in hair. After a sufficient period of time has passed to allow the permanent wave lotion to rupture at least some of the cystine sulfur to sulfur bonds in the length of hair, the length of human hair and the strip of permanent wave end paper may be saturated with a portion of the volume of permanent wave neutralizing agent for reforming the cystine sulfur to sulfur bonds that were ruptured by the permanent wave lotion. Under such an inventive method, the strip of permanent wave end paper exhibits a chromatic indication of whether the strip of permanent wave end paper and the length of hair have been saturated with the respective permanent wave liquid chemical. As a result, a user can ensure that the strip of permanent wave end paper and the length of hair have been completely saturated with the permanent wave chemical solution by ensuring that the entire strip of permanent wave end paper demonstrates a change in color in response to the application of the permanent wave liquid chemical.

Of course, additional objects and advantages of the present invention will become obvious to those skilled in the art who read this specification and view the accompanying drawings. One also should be mindful that the foregoing discussion is designed merely to outline broadly the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of possible manifestations of the invention.

DETAILED DESCRIPTION OF A PREFERRED EMBODIMENT

Figure 1:
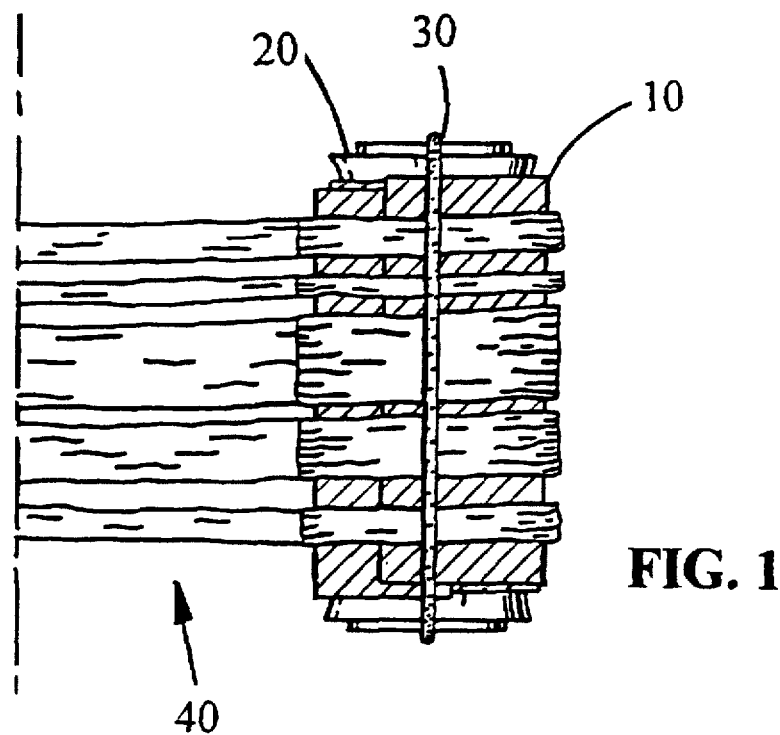
FIG. 1 is a top plan view of a length of human hair rolled onto a rod with a strip of a permanent wave end paper according to the present invention prior to application of a permanent wave liquid chemical.

Looking more particularly to the figures, there is shown in FIG. 1 a top plan view of an embodiment of the invention for a permanent wave end paper 10. The permanent wave end paper 10 is shown in normal use wherein a strip of permanent wave end paper 10 is rolled along with a distal end of a length of hair 40 that is to be permanently waved onto a permanent wave rod 20 in a manner well known to the art. An elastic restraining band 30 with opposite ends operably associated with opposite ends of the permanent wave rod 20 maintains the length of hair 40 and the permanent wave end paper 10 in a rolled condition. In practice, the permanent wave end paper 10 prevents the distal ends of the length of hair 40 from frizzing and from other types of damage due to the application of permanent wave liquid chemicals such as permanent wave lotion (not shown).

The permanent wave end paper 10 may be any fine, flexible paper that maintains its structural integrity when saturated with liquids such as water, permanent wave lotion, and permanent wave neutralizing agent. Typically, permanent wave end paper 10 is sold in small rectangular sheets that are approximately four inches wide and three inches long. However, it should be clear that the present invention for a permanent wave end paper 10 is in no way limited to any specific size or shape.

The general properties of prior art permanent wave end paper are disclosed in U.S. Pat. No. 4,655,377 to Orangeo, Jr. et al., which is incorporated herein by reference. As that patent makes clear, permanent wave end paper 10 normally comprises a high purity cellulose paper. The permanent wave end paper has a weight of approximately 16 grams per square meter and a thickness of approximately 0.02 inches. To increase the wet strength and tear resistance of the permanent wave end paper 10, the permanent wave end paper 10 is impregnated with a wet strength resin selected from the group consisting of urea formaldehyde and melamine. With such an embodiment, preferred permanent wave end paper 10 has a wet strength sufficient to withstand a tension of at least about 30 grams applied to a one-half inch wide strip of permanent wave end paper 10, and a most preferred permanent wave end paper 10 has a wet strength sufficient to withstand a tension of at least about 50 grams applied to a one-half inch wide strip of permanent wave end paper. Of course, the present invention does not depend on dimension, and the foregoing one-half inch width dimension is set forth only for strength specification. With regard to porosity, preferred permanent wave end paper 10 has a Filtrona Pressure Drop of between about 14.1 and 24.2 millimeters of water.

According to the present invention, the permanent wave end paper 10 is impregnated with a pH indicator dye that is calibrated to change color in response to an application of a permanent wave liquid chemical (i.e., permanent wave lotion or permanent wave neutralizing agent, neither of which are shown). When the permanent wave end paper 10 is associated with a length of hair 40, as is shown in FIGS. 1, 2 and 3 where the permanent wave end paper 10 is rolled along with the length of hair 40 onto a permanent wave rod 20, a user (i.e., a hairdresser) can visually ensure that the permanent wave end paper 10 and the length of hair 40 have been completely saturated with the permanent wave liquid chemical.

Figure 2:
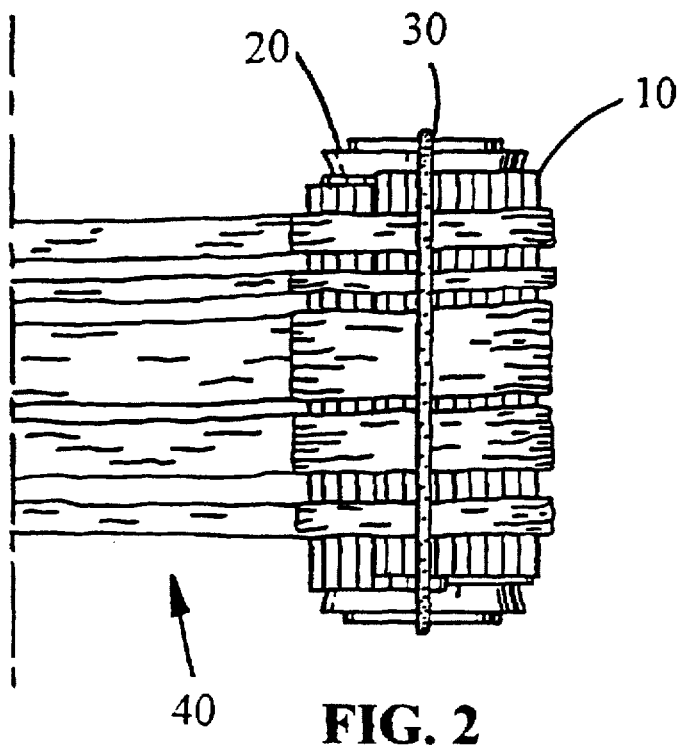
FIG. 2 is a top plan view of the length of human hair, the rod, and the strip of permanent wave end paper of FIG. 1 after complete saturation by permanent wave lotion.
Figure 3:
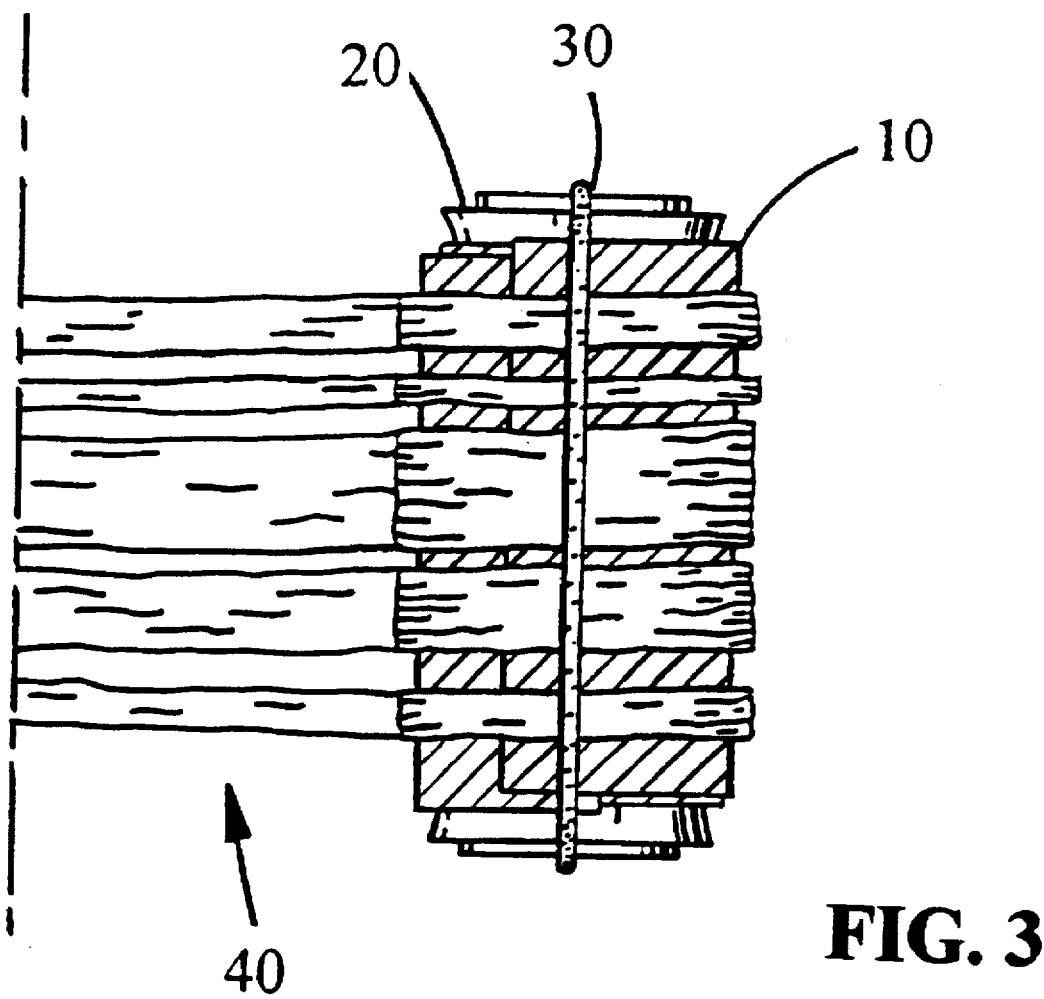
FIG. 3 is a top plan view of the length of human hair, the rod, and the strip of permanent wave end paper of FIG. 2 after complete saturation by permanent wave neutralizing agent.

To provide an example, where the pH indicator is calibrated to change from a pre-permanent-wave-lotion-saturation first color as in FIG. 1 to a post-permanent-wave-lotion-saturation second color as in FIG. 2 in response to the application of permanent wave lotion, a user can be confident that the length of hair 40 has been saturated completely by ensuring that the entire outer surface of the permanent wave end paper 10 exhibits the desired change in color; where there is not a change in color, more permanent wave lotion should be added. One skilled in the art will realize that not only does the change in color of the present invention allow a user to ensure that the length of hair 40 is completely saturated, but the color change also prevents waste of permanent wave liquid chemicals. This derives from the fact that once the entire strip of permanent wave end paper 10 has changed color, a user will realize that the application of additional permanent wave liquid chemical is redundant and wasteful. With similar benefit, the permanent wave end paper 10 changes from the second color of FIG. 2 to the third color of FIG. 3 in response to a saturation of the permanent wave end paper 10 with permanent wave neutralizing agent. To be clear, the importance of color change in this case relates to change between successive colors (i.e., first to second and second to third). It may be possible, and it is certainly within the scope of this invention, that non-successive colors (i.e., first and third colors) may be similar or identical.

To carry forth the foregoing color change pattern, one embodiment of the permanent wave end paper 10 according to the present invention is impregnated with a multiplicity of pH indicator dyes that change colors at different pH ranges whereby the permanent wave end paper 10 functions as a universal indicator paper. A typical color chart for universal indicator paper could be described as follows: Red, pH 2.0, very strong acid; Orange, pH 4.0, strongly acid; Yellow, pH 6.0, weakly acid; Green, pH 8.0, weekly alkaline; Blue, pH 10.0, strongly alkaline. With such a color change spectrum, when the permanent wave end paper 10 is associated with a length of human hair 40, the permanent wave end paper 10 changes from a first color (FIG. 1) to a second color (FIG. 2) when the permanent wave end paper 10 and length of hair 40 have been completely saturated with a permanent wave lotion, and the permanent wave end paper 10 changes from the second color (FIG. 2) to a third color (FIG. 3) in response to the application of a permanent wave neutralizing agent. These color changes in the permanent wave end paper 10 in response to the application of a permanent wave chemical solution provide a visual indication of the saturation condition of the permanent wave thereby eliminating guesswork as to the proper saturation of a length of hair 40 during a permanent wave process. Since the universal indicator permanent wave end paper 10 may be impregnated with a multiplicity of different pH indicator dyes, it should be clear that permanent wave end paper 10 may be colored or impregnated to have selected pre-permanent-wave-lotion-saturation colors and to demonstrate a variety of color changes in response to saturation with permanent wave lotion and permanent wave neutralizing agent. Such changes are of form only and are well within the scope of the present invention.

Furthermore, in light of the present disclosure, one skilled in the art will realize that the invention may be carried forth with a permanent wave end paper 10 impregnated with a single pH indicator dye. Certainly, such a permanent wave end paper 10 is within the scope of the present invention. For example, the permanent wave end paper 10 may be impregnated to great advantage with a single pH indicator dye called litmus, which is red at any pH less than 5.0 and blue at any pH greater than 8.0 thereby enabling one to determine whether a solution is acidic or basic.

A number of tests have been conducted with such a permanent wave end paper 10. These tests have shown in an acid-type permanent wave process that, when permanent wave lotion is applied to permanent wave end paper 10 that initially is red, the permanent wave end paper 10 will exhibit a color change from red as is shown in FIG. 1 to blue as is shown in FIG. 2. When the entire permanent wave end paper 10 demonstrates such a color change, a user can be confident that the entire length of human hair 40 that has been rolled with the permanent wave end paper 10 has been saturated. Similarly, when using an alkaline-type permanent wave lotion, a color change of from red to blue will occur upon application of the permanent wave lotion. When the permanent wave neutralizing agent is applied to the permanent wave end paper 10 in an acid-type permanent wave process, the hairdresser will observe a color change from blue as in FIG. 2 to a pale shade of red (i.e., pink) as is shown in FIG. 3 or to white. In an alkaline-type permanent wave process, a color change from blue to white or to a pale shade of blue will occur when the permanent wave neutralizing agent is applied to the permanent wave end paper 10 and the length of hair 40.

Hairdressing techniques are described in detail in "Perming ... Beyond Great Curl technical source book", which is incorporated herein by reference (copyright 1993 by Matrix Essentials, Inc., Solon, Ohio 44139), on pages 76 to 83 while the details of hair anatomy, the chemical and physical forces in permanent waving, and the alkaline and acid waves are included on p.2 to p. 7 of the same reference. Essentially, the basic hairdressing techniques described therein are followed in practicing the method of the present invention. However, the permanent wave end paper 10 of the instant invention is used in place of using white, non-impregnated permanent wave end paper of the prior art, which disadvantageously does not allow a hairdresser to determine visually whether a permanent wave liquid chemical has thoroughly saturated the permanent wave end paper 10 and a length of hair 40.

In any event, the present inventive method of permanently waving hair begins with providing a volume of a permanent wave lotion for rupturing cystine sulfur to sulfur bonds that are found in hair, providing a volume of a permanent wave neutralizing agent for reforming the cystine sulfur to sulfur bonds that were ruptured by the permanent wave lotion, and providing a plurality of strips of permanent wave end paper 10 that comprises an absorbent paper impregnated with a pH indicator that is calibrated to change color in response to an application of a permanent wave liquid chemical such as the permanent wave lotion and/or the permanent wave neutralizing agent. With such a kit of materials available, one practicing the invention arranges a length of hair 40 in a desired configuration and disposes a strip of permanent wave end paper 10 against a length of hair 40 to be permanently waved. Normally, arranging the length of hair 40 in a desired configuration comprises rolling the length of hair 40 and the permanent wave end paper 10 onto a permanent waving rod 20. With the permanent wave end paper 10 associated with the length of hair 40, the length of hair 40 and the strip of permanent wave end paper 10 are saturated with at least a portion of the volume of permanent wave lotion. A sufficient period of time is then allowed to pass to allow the permanent wave lotion to rupture at least some of the cystine sulfur to sulfur bonds in the length of hair 40. Then the length of hair 40 and the strip of permanent wave end paper 10 is saturated with at least a portion of the volume of permanent wave neutralizing agent. With this embodiment of the inventive permanent wave method, the strip of permanent wave end paper 10 exhibits a chromatic indication of whether the strip of permanent wave end paper 10 and the length of hair 40 to be permanently waved have been saturated with the respective permanent wave liquid chemical, and a user can ensure that the strip of permanent wave end paper 10 and the length of hair 40 have been completely saturated with the permanent wave liquid chemical by ensuring that the entire strip of permanent wave end paper 10 demonstrates a change in color in response to the application of the permanent wave liquid chemical.

As the foregoing makes clear, the present invention provides the user with a multiplicity of advantages. For example, the invention provides a permanent wave end paper 10 and a method of use thereof that allows a person to determine visually whether a strip of permanent wave end paper 10 and a length of hair 40 with which the permanent wave end paper 10 is associated are saturated by a permanent wave liquid chemical by demonstrating a color change upon the application of a permanent wave lotion and a neutralizing agent. As a result, the permanent wave end paper 10 and the method of use thereof prevent waste of permanent wave liquid chemical by indicating to a user when a strip of permanent wave end paper 10 and a length of hair 40 are saturated with the permanent wave liquid chemical. Furthermore, the permanent wave end paper 10 eliminates unnecessary guesswork from the permanent wave process by allowing a user to ensure easily that the permanent wave end paper 10 and the length of human hair 40 are completely saturated with the respective permanent wave liquid chemical. As a result, resulting permanent waves are improved, and the quality, reliability, and convenience of the permanent wave process is enhanced. Such benefits inevitably will improve the actual and apparent efficiency and skill of the hairdresser using the invention. Certainly of equal importance is that the permanent wave end paper 10 is simple in design and manufacture and, consequently, inexpensive to develop. Still further, the invention enjoys a wide scope of application as it may be used in hair salons, by beauticians as a teaching tool in beauty schools, and in animal grooming.

Although the invention has been shown and described with reference to certain preferred embodiments, those skilled in the art undoubtedly will find alternative embodiments obvious after reading this disclosure. With this in mind, the following claims are intended to define the scope of protection to be afforded the inventor, and those claims shall be deemed to include equivalent constructions insofar as they do not depart from the spirit and scope of the present invention.

I claim as protected by United States Letters Patent:

1. A permanent wave end paper comprising an absorbent paper impregnated with a pH indicator wherein the permanent wave end paper is calibrated to change color in response to an application of a permanent wave liquid chemical when the permanent wave liquid chemical is applied to the permanent wave end paper whereby, when the permanent wave end paper is associated with a length of hair to be permanently waved, the permanent wave end paper exhibits an immediate chromatic indication of whether the permanent wave end paper and the length of hair have been saturated with the permanent wave liquid chemical whereby a user can ensure that the permanent wave end paper and the length of hair have been completely saturated with the permanent wave liquid chemical by ensuring that the entire strip of permanent wave end paper demonstrates an immediate change in color in response to the application of the permanent wave liquid chemical.

2. The permanent wave end paper of claim 1 wherein the permanent wave end paper has a wet strength sufficient to withstand a tension of at least about 30 grams applied to a one-half inch wide strip of permanent wave end paper.

3. The permanent wave end paper of claim 2 wherein the pH indicator comprises litmus dye whereby, when the permanent wave end paper is associated with a length of hair to be permanently waved, the permanent wave end paper changes from a first color to a second color when the permanent wave end paper and the length of hair are saturated with a permanent wave lotion and the permanent wave end paper changes from the second color to a third color when the permanent wave end paper and the length of hair are saturated with a permanent wave neutralizing agent.

4. The permanent wave end paper of claim 2 wherein the permanent wave end paper is impregnated with a multiplicity of different pH indicator dyes wherein a first pH indicator dye is calibrated to exhibit a chromatic indication when the permanent wave end paper is saturated with a permanent wave lotion and a second indicator dye is calibrated to exhibit a chromatic indication when the permanent wave end paper is saturated with a permanent wave neutralizing agent such that the permanent wave end paper comprises a universal indicator paper whereby, when the permanent wave end paper is associated with a length of hair to be permanently waved, the permanent wave end paper changes from a first color to a second color when the permanent wave end paper and the length of hair are saturated with a permanent wave lotion and the permanent wave end paper changes from the second color to a third color when the permanent wave end paper and the length of hair are saturated with a permanent wave neutralizing agent.

5. The permanent wave end paper of claim 1 wherein the absorbent paper comprises a high purity cellulose paper.

6. The permanent wave end paper of claim 5 wherein the permanent wave end paper is further impregnated with a wet strength resin for increasing a wet strength and a tear resistance of the permanent wave end paper.

7. The permanent wave end paper of claim 6 wherein the wet strength resin is selected from the group consisting of urea formaldehyde and melamine.

8. The permanent wave end paper of claim 1 wherein the permanent wave end paper has a thickness not greater than about 0.02 inches.

9. The permanent wave end paper of claim 8 wherein the permanent wave end paper has a weight of approximately 16 grams per square meter and a Filtrona Pressure Drop when non-perforated of between about 14.1 and 24.2 millimeters of water.

10. A kit for imparting a permanent wave to hair, the kit comprising in combination:
  a) a permanent wave lotion for being applied to hair to cause rupture of cystine sulfur to sulfur bonds found in hair fibers;
  b) a permanent wave neutralizing agent for being applied to hair after the permanent wave lotion to reform the cystine sulfur to sulfur bonds that were ruptured by the permanent wave lotion; and
  c) at least one strip of permanent wave end paper comprising an absorbent paper impregnated with a pH indicator wherein the permanent wave end paper is calibrated to change color in response to an application of a permanent wave liquid chemical when the permanent wave liquid chemical is applied to the permanent wave end paper whereby, when a length of hair to be permanently waved is rolled with the at least one strip of the permanent wave end paper, the at least one strip of permanent wave end paper exhibits an immediate chromatic indication of whether the at least one strip of permanent wave end paper and the length of hair have been saturated with a permanent wave liquid chemical when the permanent wave liquid chemical is applied to the permanent wave end paper and a user can ensure that the permanent wave end paper and the length of hair have been completely saturated with the permanent wave liquid chemical by ensuring that the entire strip of permanent wave end paper demonstrates an immediate change in color in response to the application of the permanent wave liquid chemical.

11. The permanent wave kit of claim 10 wherein the at least one strip of permanent wave end paper has a wet strength sufficient to withstand a tension of at least about 30 grams applied to a one-half inch wide strip of permanent wave end paper.

12. The permanent wave kit of claim 10 wherein the at least one strip of absorbent paper comprises a high purity cellulose paper.

13. The permanent wave kit of claim 12 wherein the at least one strip of permanent wave end paper is further impregnated with a wet strength resin for increasing a wet strength and a tear resistance of the at least one strip of permanent wave end paper.

14. The permanent wave kit of claim 10 wherein the permanent wave end paper has a thickness not greater than about 0.02 inches.

15. The permanent wave kit of claim 10 wherein the pH indicator comprises litmus dye whereby, when the at least one strip of permanent wave end paper is associated with a length of hair to be permanently waved, the at least one strip of permanent wave end paper changes from a first color to a second color when the at least one strip of permanent wave end paper and the length of hair are saturated with a permanent wave lotion and the at least one strip of permanent wave end paper changes from the second color to a third color when the at least one strip of permanent wave end paper and the length of hair are saturated with a permanent wave neutralizing agent.

16. The permanent wave kit of claim 10 wherein the at least one strip of permanent wave end paper is impregnated with a multiplicity of different pH indicator dyes wherein a first pH indicator dye is calibrated to exhibit a chromatic indication when the permanent wave end paper is saturated with a permanent wave lotion and a second indicator dye is calibrated to exhibit a chromatic indication when the permanent wave end paper is saturated with a permanent wave neutralizing agent such that the permanent wave end paper comprises a universal indicator paper whereby, when a length of hair to be permanently waved is rolled with the at least one strip of permanent wave end paper, the at least one strip of permanent wave end paper changes from a first color to a second color when the at least one strip of permanent wave end paper and the length of hair are saturated with a permanent wave lotion and the at least one strip of permanent wave end paper changes from the second color to a third color when the at least one strip of permanent wave end paper and the length of hair are saturated with a permanent wave neutralizing agent.

17. A method for permanently waving hair comprising the steps of:
  a) providing a volume of a permanent wave lotion for rupturing cystine sulfur to sulfur bonds that are found in hair;
  b) providing a volume of a permanent wave neutralizing agent for reforming the cystine sulfur to sulfur bonds that were ruptured by the permanent wave lotion;
  c) providing at least one strip of permanent wave end paper wherein the at least one strip of permanent wave end paper comprises an absorbent paper impregnated with a pH indicator wherein the at least one strip of permanent wave end paper is calibrated to change color in response to an application of a permanent wave liquid chemical when the permanent wave liquid chemical is applied to the permanent wave end paper;

d) disposing the at least one strip of permanent wave end paper against a length of hair to be permanently waved;

e) arranging the length of hair in a desired configuration;

f) saturating the length of hair and the at least one strip of permanent wave end paper with a portion of the volume of permanent wave lotion;

g) ensuring that the at least one strip of permanent wave end paper exhibits an immediate chromatic indication over the entire at least one strip of permanent wave end paper in response to saturation with the permanent wave lotion;

h) allowing a sufficient period of time to pass to allow the permanent wave lotion to rupture at least some of the cystine sulfur to sulfur bonds in the length of hair; and i) saturating the length of hair and the at least one strip of permanent wave end paper with a portion of the volume of permanent wave neutralizing agent;

j) ensuring that the at least one strip of permanent wave end paper exhibits an immediate chromatic indication over the entire at least one strip of permanent wave end paper in response to saturation with the permanent wave neutralizing agent;

k) whereby the at least one strip of permanent wave end paper exhibits an immediate chromatic indication of whether the at least one strip of permanent wave end paper and the length of hair to be permanently waved have been saturated with the permanent wave liquid chemical and a user can ensure that the at least one strip of permanent wave end paper and the length of hair have been completely saturated with the permanent wave liquid chemical by ensuring that the entire at least one strip of permanent wave end paper demonstrates an immediate change in color in response to the application of the permanent wave liquid chemical.

18. The method of claim 17 wherein the step of providing at least one strip of permanent wave end paper comprises providing at least one strip of permanent wave end paper each with a wet strength sufficient to withstand a tension of at least about 30 grams applied to a one-half inch wide strip of the permanent wave end paper.

19. The method of claim 18 wherein the step of providing at least one strip of permanent wave end paper comprises providing at least one strip of high purity cellulose paper.

20. The method of claim 19 wherein the step of providing at least one strip of permanent wave end paper comprises providing at least one strip of permanent wave end paper that is further impregnated with a wet strength resin for increasing a wet strength and a tear resistance of the strips of permanent wave end paper.

21. The method of claim 20 wherein the step of providing at least one strip of permanent wave end paper comprises providing at least one strip of permanent wave end paper wherein the wet strength resin is selected from the group consisting of urea formaldehyde and melamine.

22. The method of claim 20 wherein the step of providing at least one strip of permanent wave end paper comprises providing at least one strip of permanent wave end paper with a wet strength sufficient to withstand a tension of at least about 50 grams applied to a one-half inch wide strip of permanent wave end paper.

23. The method of claim 17 wherein the step of providing at least one strip of permanent wave end paper comprises providing at least one strip of permanent wave end paper wherein the pH indicator comprises litmus dye whereby, when the at least one strip of permanent wave end paper is associated with a length of hair to be permanently waved, the at least one strip of permanent wave end paper changes from a first color to a second color when the at least one strip of permanent wave end paper and the length of hair are saturated with a permanent wave lotion and the at least one strip of permanent wave end paper changes from the second color to a third color when the at least one strip of permanent wave end paper and the length of hair are saturated with a permanent wave neutralizing agent.

24. The method of claim 17 wherein the step of providing at least one strip of permanent wave end paper comprises providing at least one strip of permanent wave end paper that is impregnated with a multiplicity of different pH indicator dyes wherein a first pH indicator dye is calibrated to exhibit a chromatic indication when the permanent wave end paper is saturated with a permanent wave lotion and a second indicator dye is calibrated to exhibit a chromatic indication when the permanent wave end paper is saturated with a permanent wave neutralizing agent such that the at least one strip of permanent wave end paper changes from a first color to a second color when the at least one strip of permanent wave end paper and the length hair to be permanently waved are saturated with the permanent wave lotion and the at least one strip of permanent wave end paper changes from the second color to a third color when the at least one strip of permanent wave end paper and the length of hair to be permanently waved are saturated with a permanent wave neutralizing agent.

* * * * *